US012585057B2

(12) United States Patent
Bergsten et al.

(10) Patent No.: US 12,585,057 B2
(45) Date of Patent: Mar. 24, 2026

(54) LIGHT DIFFUSER AND A METHOD FOR ASSEMBLING THE SAME

(71) Applicant: Neola Medical AB, Lund (SE)

(72) Inventors: Sara Bergsten, Lund (SE); Dennis Leander, Malmo (SE)

( * ) Notice: Subject to any disclaimer, the term of this patent is extended or adjusted under 35 U.S.C. 154(b) by 0 days.

(21) Appl. No.: 17/906,827

(22) PCT Filed: Mar. 17, 2021

(86) PCT No.: PCT/EP2021/056751
§ 371 (c)(1),
(2) Date: Sep. 20, 2022

(87) PCT Pub. No.: WO2021/185880
PCT Pub. Date: Sep. 23, 2021

(65) Prior Publication Data
US 2023/0083665 A1 Mar. 16, 2023

(30) Foreign Application Priority Data
Mar. 20, 2020 (SE) ..................................... 2030094-3

(51) Int. Cl.
*F21V 8/00* (2006.01)
*A61N 5/06* (2006.01)
*G02B 5/02* (2006.01)

(52) U.S. Cl.
CPC .......... *G02B 6/0055* (2013.01); *G02B 6/0011* (2013.01); *G02B 6/0028* (2013.01); *G02B 6/0051* (2013.01); *A61N 5/0616* (2013.01); *G02B 5/0231* (2013.01)

(58) Field of Classification Search
CPC .. G02B 6/0011; G02B 6/0028; G02B 5/0231; G02B 6/0051; A61N 5/0614–0625; G02F 1/133526
See application file for complete search history.

(56) References Cited

U.S. PATENT DOCUMENTS

| | | | |
|---|---|---|---|
| 5,521,797 A | 5/1996 | Kashima et al. | |
| 6,259,496 B1 | 7/2001 | Kashima | |
| 2007/0025121 A1* | 2/2007 | Harada | G02B 6/0053 |
| | | | 362/606 |
| 2007/0239232 A1 | 10/2007 | Kurtz | |

(Continued)

FOREIGN PATENT DOCUMENTS

| | | |
|---|---|---|
| EP | 0761257 A2 | 3/1997 |
| EP | 2881766 A1 | 6/2015 |

(Continued)

OTHER PUBLICATIONS

International Search Report and Written Opinion, Application No. PCT/EP2021/056751, mailed Jun. 15, 2021, 12 pages.

(Continued)

*Primary Examiner* — Jessica M Merlin

(57) ABSTRACT

A device and method for providing diffuse emission of light through a flat surface, which includes a flat light guide having two larger flat surfaces on opposite sides and side surfaces, wherein one of the two larger flat surfaces being a light emitting surface and the other surface being a back surface, a connector for coupling light into said flat light guide, and a diffusing layer arranged in contact with at least one of said two larger flat surfaces of said flat light guide.

12 Claims, 6 Drawing Sheets

(56) References Cited

U.S. PATENT DOCUMENTS

| | | | | | |
|---|---|---|---|---|---|
| 2009/0067190 | A1 | | 3/2009 | Funabashi | |
| 2010/0160754 | A1 | | 6/2010 | Durkin | |
| 2012/0294037 | A1 | * | 11/2012 | Holman | G02B 6/0061 |
| | | | | | 362/628 |
| 2012/0320628 | A1 | | 12/2012 | Chang | |
| 2014/0233258 | A1 | * | 8/2014 | Zhang | G02B 6/005 |
| | | | | | 362/606 |
| 2015/0062871 | A1 | * | 3/2015 | Kim | G02B 5/0231 |
| | | | | | 362/355 |
| 2016/0070052 | A1 | | 3/2016 | Masuda | |
| 2019/0285935 | A1 | * | 9/2019 | Tan | G02F 1/133526 |
| 2019/0391449 | A1 | | 12/2019 | Hao | |
| 2020/0110213 | A1 | * | 4/2020 | Shiba | G02B 6/0061 |

FOREIGN PATENT DOCUMENTS

| | | | | | |
|---|---|---|---|---|---|
| KR | 20020047653 | A | * | 6/2002 | |
| KR | 20080087943 | A | | 10/2008 | |
| KR | 20110071037 | A | * | 6/2011 | G02B 6/0045 |
| WO | WO2019077375 | A1 | | 4/2019 | |

OTHER PUBLICATIONS

Swedish Office Action, Application No. 2030094-3, dated Nov. 19, 2020, 9 pages.
Extended European Search Report received in European Application No. 24200639.3, mailed on Mar. 11, 2025, 07 pages.

* cited by examiner

150

190

14

3     6

200

101

102

103

LIGHT DIFFUSER AND A METHOD FOR ASSEMBLING THE SAME

PRIORITY INFORMATION

This application is a U.S. National Phase Application of PCT Application No.: PCT/EP2021/056751, filed Mar. 17, 2021, which claims priority to Sweden Application No.: 2030094-3, filed Mar. 20, 2020.

BACKGROUND OF THE INVENTION

Field of the Invention

This disclosure pertains to a device for diffusing light and a method for assembling or manufacturing the same, in particular a light diffuser having a flat light emitting surface is described herein. The device is especially designed for spreading out the light over an area of said diffuser and to optimize the amount of light transmitted from the diffuser to a material arranged in contact with the light emitting surface, in particular the diffuser is designed for dermal use.

Description of the Prior Art

There are many different types of light diffusing technologies available to be used in the field of spectroscopy. Many of them are used for obtaining a cylindrical light distribution and could be either a light diffuser tip to be connected to an end of a fiber or a writing in the core or cladding of the fiber itself.

In some application, flat light diffusers may be of interest. Most flat diffusers may be found in the area of LED displays and are not suitable to be used for spectroscopy, especially not for coupling light between the diffuser and a material arranged in contact with a diffusing surface.

There are also very few flat light diffusers designed to be used in the medical technology filed, such as dermal use.

Hence, a new light diffuser and a method for manufacturing the same, designed for use in the field of spectroscopy, could be advantageous. In particular, a flat light diffuser optimized for providing an high transmission and a good coupling between a light emitting surface and a material in contact with the surface to allow a high transmission of light between the light emitting surface of the diffuser and the material, could be advantageous. Especially, a flat diffuser configured to be used in the medical field, such as dermal use, would be an advantage. It would also be an advantage to provide a flat light diffuser which is easy and cost effective to manufacture.

SUMMARY OF THE DISCLOSURE

Embodiments of the present disclosure preferably seek to mitigate, alleviate or eliminate one or more deficiencies, disadvantages or issues in the art, such as the above-identified, singly or in any combination by providing a device, and/or method according to the description.

According to one aspect of the disclosure, a device for providing diffuse emission of light through a flat surface is described. The device includes a flat light guide having two larger flat surfaces on opposite sides and side surfaces, wherein one of the two larger flat surfaces being a light emitting surface and the other surface being a back surface. The device may further include a connector for coupling light into the flat light guide and also a diffusing layer arranged in contact with at least one of the two larger flat surfaces of the flat light guide.

In some examples of the disclosure the device includes a reflective material arranged on all sides of the flat light guide, apart from the light emitting surface.

In some examples of the disclosure, the reflective material may reflect light either through specular reflection or through diffuse reflection.

In some examples of the disclosure, the diffusing layer may be arranged between the back surface and the reflective material.

In some examples of the disclosure, the diffusing layer may have a refractive index higher than the flat light guide.

In some examples of the disclosure, the diffusing layer may be printed on one of the two larger flat surfaces of the flat light guide.

In some examples of the disclosure, the diffusing layer may be arranged as a pattern on one of the two larger flat surfaces of the flat light guide to provide a plurality of areas of diffuse reflection.

In some examples of the disclosure, the pattern may be printed as a plurality of areas of various widths and space between.

In some examples of the disclosure, the diffusing layer may include structures, such as microstructures, to diffuse the light. Alternatively and/or additionally, the diffusing layer may be a structural writing on at least one of the two larger surfaces of the flat light guide.

In some examples of the disclosure, the diffusing layer may be arranged as the pattern on the back surface of the flat light guide and the reflective layer is reflecting light of areas of the back surface not covered by the pattern.

In some examples of the disclosure, the light emitting surface may be covered by a first layer having a lower refractive index than the flat light guide.

In some examples of the disclosure, the layer covering the light emitting surface may have a refractive index close to a material, such as human skin, to which light should be coupled.

In some examples of the disclosure, the diffusing layer may be arranged on the light emitting surface, or is arranged in the light guide, and a second layer may be arranged on the back surface and the side surfaces. The second layer may have a lower refractive index than the flat light guide.

In some examples of the disclosure, the diffusing layer may be arranged on the back surface and a second layer may be arranged on top of the diffusing layer and on the side surfaces has a lower refractive index than the flat light guide.

In some examples of the disclosure, the diffusing layer may be arranged on the back surface and the second layer may be arranged between the diffusing layer and the reflecting layer.

In some examples of the disclosure, an initial area closest to the connector may not be covered by the diffusing material.

According to one aspect of the disclosure, a method of manufacturing a device for providing diffuse emission of light through a flat surface is described. The method may include providing a flat light guide having two larger flat surfaces on opposite sides and side surfaces, wherein one of the two larger flat surfaces being a light emitting surface and the other surface being a back surface. The method may also include, arranging a connector for coupling light into the flat light guide, and arranging a diffusing layer in contact with at least one of the two larger flat surfaces of the flat light guide.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which examples of the disclosure are capable of will be apparent and elucidated from the following description of examples of the present disclosure, reference being made to the accompanying drawings, in which.

DESCRIPTION OF EXAMPLES

Specific examples of the disclosure will now be described with reference to the accompanying drawings. This disclosure may, however, be embodied in many different forms and should not be construed as limited to the examples set forth herein; rather, these examples are provided so that the disclosure will be thorough and complete, and will fully convey the scope of the disclosure to those skilled in the art.

The inventors have found a way of providing a flat diffuser that spreads out the light power over a light emitting surface and has a high coupling of light out from a light emitting area of the diffuser to a material in contact with the light emitting surface. The diffuser may provide increased eye safety, such as laser class 1, during spectroscopy measurements and reduce issues with heating effects, such as hotspots. Avoiding hotspots is important in many applications of spectroscopic measurements. One such example may be measurements of tissue, in which the temperature should be kept below 42 degrees Celsius to avoid cell damages. The diffuser is further characterized by a high power output in comparison to the light power coupled into the diffuser. Most of the light coupled into the diffuser may therefore be transmitted out e.g. the diffuser has a low absorption of light and/or the diffuser may have low losses through other surfaces than a light emitting surface and/or the light may be coupled back through the inlet. Measurements and simulation have shown that the transmission of light to the underlying material could be around 85% of the light coupled into the diffuser. The diffuser does not have any gas inside, thus there is no gas footprint which may affect the spectroscopic measurements by gas spectroscopy. The diffuser further allows it to easily couple in light from an optical source, such as an optical fiber.

The diffuser is rigid enough not to break during spectroscopic measurements, such as when arranged on the body of a patient.

The main concept is to couple light into a transparent light guide in which the light is trapped by total reflection until it hits a part of the light guide which changes the angle of the reflected light. Thereby may the light be able to exit the light guide.

Figures 1A, 1B, 2:
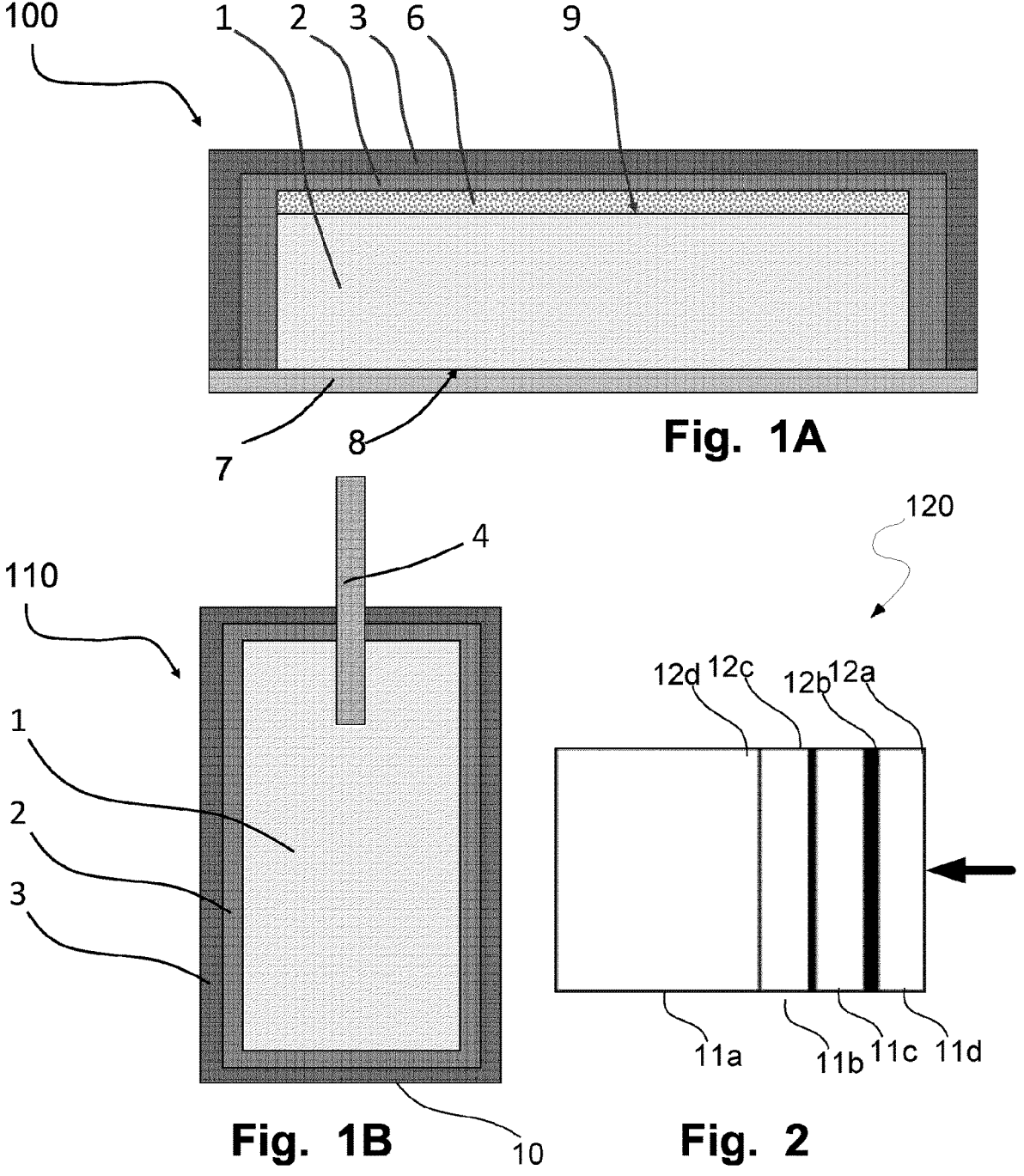
FIGS. 1A and 1B are illustrating a schematic example of a disclosed device and the layers thereof.
FIG. 2 is illustrating a schematic example of a pattern of a diffusing layer.

FIG. 1A is illustrating a schematic example of the layers of the diffuser 100. The diffuser 100 comprises a flat light guide 1 which comprises two larger surfaces opposite each other, a light emitting surface 8 and a back surface 9. The flat light guide 1, also includes thinner side surfaces. The flat waveguide may be made from a transparent material and the light coupled into the light guide 1 is trapped by total internal reflection. The material for the light guide 1 may be a plastic material, such as polycarbonate (PC), Polyethylene Terephthalate (PET) or Polymethyl Methacrylate (PMMA). For the particular configuration for dermal use described herein, PC and PET has an advantage since the refractive index is higher than for PMMA. The refractive indices of PC and PET are about 1.57 @ 760 nm and about 1.575 @ 589 nm respectively while PMMA has about 1.485 @ 760 nm. But for other configurations, PMMA may be an option.

A difference between the refractive index of the flat light guide 1 and a material surrounding the flat light guide 1, where the light guide 1 has a higher refractive index than the material surrounding the flat light guide 1, provides for the total internal reflection. Total internal reflection is provided by having a difference between the two reflective indices large enough so that the angle of the light entering the flat light guide 1 is larger than the critical angle based on Snell's law. The angle of the light entering the flat light guide depends on the numerical aperture of the light source, such as the optical fiber connected to the flat light guide 1 or LED coupled directly to the side of the light guide 1.

The diffuser 100, further includes a diffusing layer 6. The diffusing layer 6 may be either arranged on the light emitting surface 8 and/or on the back surface 9. If the diffusing layer is arranged on the light emitting surface 8, the diffusing layer 6 has to be transparent to the wavelength used to permit light to emit out of the diffuser 100. Examples of transparent diffusing layers 6 that could be applied on either the light emitting surface 8 or the back surface 9, may for example be structural writings on the light emitting surface 8. The structural writings may be made mechanically or by a laser. The structural writing will provide microstructures on or close to the light emitting surface 8. If a layer is used, a polymer with microstructures can be applied. The microstructures achieved by the structural writing or added by a polymer may be designed and form a pattern that provides the characteristics of spreading the light over the area of the light emitting surface 8. For example, the density, size and shape of the microstructures may be varied.

In the illustrated example, the diffusing layer 6 is a printed pattern made from a light scattering material, such as white paint or printed ink, applied or printed directly onto the back surface 9. Printing in directly onto the back surface 9 is a fast and cost-efficient way of obtaining a diffusing layer 6, especially for producing a larger number of diffusers. The angle of the light reflected inside the light guide 1 may change when reflected by the diffusing layer 6. The light reflected by the diffusing layer 6 may obtain an angle that will not give total internal reflection, i.e. the angle is less than the critical angle based on Snell's law, and thereby may the light be able to exit the light guide 1 through the light emitting surface 8.

The diffusing layer 6 should have a refractive index which is the same as (or at least very close to) or higher than the refractive index of the light guide 1. For the application of printing a pattern onto the light guide 1, one such material is printer ink, for example Canon IJC257 has a refractive index of 1.8, but this is only an example of many other similar materials available on the marked.

The diffuser 100 may also include a first layer 2 having a refractive index lower than the flat light guide 1. The first layer 2 may be arranged on top of the diffusing layer 6 but in some examples the first layer 2 may surround all surfaces of the light guide 1. In some examples the first layer 2 is surrounding all surfaces of the light guide 1 except for the light emitting surface 8. The first layer 2 is applied to provide a high degree of internal reflection, thus the refractive index is lower than for the light guide 1. The difference between the first layer 2 and the light guide 1 should be large enough so that total internal reflection will be observed for, at least, most of light entering the light guide 1. The light entering the light guide 1 may have angle which depends on the numeric aperture member coupling the light into the side of the light guide 1, such as a wave guide which may be an optical fiber, or a LED coupled directly to the side of the light guide 1.

The diffuser 100 may also include a reflective layer 3, the reflective layer 3 may coat all surfaces of the light guide 1, expect for the light emitting surface 8. For example, the reflective surface may be applied directly on to the diffusing layer 6 and the side surfaces. In some examples the first layer 2 is arranged between the diffusing layer 6 and the reflective layer 3, in some further examples, the first layer 2 may be applied between the side surfaces of the light guide 1 and the reflective surface 3. The reflective layer 3 is used to reflect light back into the light guide 1 which did not reflect by total internal reflection. Thereby reducing the light losses and increasing the light intensity inside the light guide 1, which in the end increases the output from the light emitting surface 8. The first layer 2 may be used as an adhesive to adhere the reflective layer 3 to the back and sides of the light guide 1.

The reflective layer 3 may reflect the light either by specular reflection, as from a metallic surface, or by diffuse reflection, such as by a white painted surface. Examples of material that may be used for the reflective layer 3 are metals such as copper-tape, chrome-tape, and aluminum foil etc., a reflective coating, such as white paint or silver paint. The reflective layer 3, may be made from a single type of reflective material or a combination thereof, for example, wherein different materials are used on different surfaces. An example of this may be a metal, such a copper-tape, added to an edge surface 10 (see FIG. 1B) opposite a side where the light is coupled into the light guide 1, while the other surfaces are coated with a reflective material, such as white paint. It is important to have a good reflection at a surface opposite where the light is coupled into the light guide 1, such as at the edge surface 10. This is important as some of the light entering the light guide 1 may not enter with an angle and will be transmitted straight through the light guide 1 without any reflection. If this light is not trapped inside the light guide 1, it may lead to losses or generate an intensity hotspot.

Preferably all surfaces, except for the light emitting surface 8, are cover by a metal, such as copper tape, chrome tape or aluminum foil.

When applying the reflective layer 3, it is important to apply it evenly to avoid inconsistencies in the surface, such as creases, or air bubbles, or uneven thickness of a paint etc. A reflective layer 3 applied uneven to the surfaces of the light guide 1, especially when it comes to metals, may give a different angle for the refractive light than the angle of the incident light, and therefore may total internal reflection no longer be obtained. Another issues is that air may be trapped in bubbles or creases of the reflective layer, which may cause problems when performing spectroscopic measurements as absorption features from the gas may be seen in the spectra. If the incident angle is different from the refractive angle, the light may not be transmitted back into the light guide 1, thus the light may be trapped between the reflective layer 3 and the light guide 1.

Depending on the use and the refractive index of the material into which the light should be coupled, the emitting surface 8 may not have a further layer.

If it has a layer 7 arranged on the light emitting surface 8, the layer 7 may be the same as the first layer 2. Alternatively, the layer 7 may be a second layer 7 made from a different material arranged on the light emitting surface 8. The second layer 7 should have a refractive index lower than the light guide 1 to provide total internal reflection for light which has not been diffused. The second layer 7 should have a refractive index which is close to the underlying material to maximize the transmission for light which exits the light guide 1 through the light emitting surface 8 into the underlying material, i.e. provide an index matching.

The second layer 7, may in some examples be a material having layers of various refractive indexes.

The second layer 7 may, in some examples, also be used to adhere the diffuser to the underlying material to be measured. This may not only have the advantage of providing a better refractive index matching but also provide the advantage of minimizing the likelihood of any gas, such as air, between the diffuser and the underlying material.

For dermal use, the applicant has found that a trilaminate, such as a transparent trilaminate with an acrylic adhesive towards the diffuser and a silicone based adhesive towards the skin, used for as an adhesive tape in health care may be a good second layer 7, especially as it also helps to adhere the diffuser to the skin. The trilaminate has an upper adhesive with a refractive index of about 1.474 at a wavelength of 633 nm, so a large difference compared to the light guide 1, and a lower adhesive having a refractive index of about 1.45 which is close to the refractive index of skin, which is about 1.4. Between the two adhesives is a carrier with a refractive index of about 1.48. Other type of material or laminates may also be possible, as long as it fulfils the criteria of having a top surface with a refractive index lower than the light guide 1 and a bottom layer having refractive index close to the material into which the light should be coupled.

On top of the layers illustrated in FIG. 1A may a housing be arranged to further protect the diffuser 100. The housing may, for example, be 3D-printed or a cast made from cured resin shaped using a mold.

FIG. 1B is illustrating a schematic example of a disclosed device 110 for diffusing light and at least some of its components. In the illustrated example, the light emitting surface is seen. The diffuser comprises a flat light guide 1. The flat light guide 1 is configured as a diffuser plate. The illustrated flat diffuser 110 may further comprise a first layer 2 surrounding all surfaces of the flat light guide 1, expect for the light emitting surface. Further, a diffusing layer (not seen in this figure) may be arranged between the first layer 2 and the light guide 1 on a back surface of the light guide 1. Alternatively, the diffusing layer may be arranged between the light emitting surface and the second layer 7. In another alternative, the diffusing layer is part of the flat light guide 1, such as incorporated microstructures.

The first layer 2 may be a polymer film, such as an adhesive polymer film. The first layer 2 may have a refractive index lower than the flat light guide 1, such as the diffuser plate. By having a lower refractive index of the first layer 2, reflectance is increased, and more light is trapped inside the flat light guide 1 due to total internal reflectance, as described earlier in relation to FIG. 1A. The illustrated example may further include a reflective material, illustrated in FIG. 1B, covering the back side and the sides of the light wave guide 1.

In the illustrated example, is the light diffuser 110 connected to a waveguide 4, such as an optical fiber, to couple light from a light source into the flat light guide 1 from a side, along the waveguide. When using a waveguide 4, as illustrated, the area of the light emitting surface of the diffuser 110 is preferably larger than an area of a cross-section of the waveguide 4. The ratio between the area of the light emitting surface and the cross-section of the waveguide could be larger than 3, such as larger than 5.

Alternatively, in some examples could LED light sources be used to couple light directly into the side of the light diffuser 110. The light from the LED light sources may be coupled into the flat light guide without the use of any waveguide, such as an optical fiber.

FIG. 2 is illustrating a schematic example of a pattern 120 for diffusing layer. The diffusing layer is made from a diffusing material. In some examples may the diffusing material be painted or printed onto the light guide. One such material that may be printed or painted onto the flat wave guide is a diffusing white paint. An arrow is illustrating the side from which the light is entering the light guide. The pattern 120 is an example of patterns to be used for spreading light over a larger area in the light guide and to provide a more even light distributions from the emitting surface with a minimized number of areas with spikes or hotspots in the intensity. The pattern is made from diffusing layers arranged as areas, such as stripes, 11a-d of varying widths. The areas may be arranged along the length of the flat light guide and each area may have a length which is the same as a width of the flat light guide. Between the diffusing areas 11a-d, there will be areas arranged with, such as stripes, with no diffusing material 12a-d. In these areas the light will be reflected by total internal reflection. These areas made from no diffusing material may also have varied widths and may have a length which is the same as a width of the flat light guide. Hence, the pattern provides that the light coupled into the light guide is trapped by total internal reflection until it hits a part of the light guide with a diffusing layer which will changes the angle of the light and provide a possibility for the light of exiting the light guide through the light emitting surface.

If no diffusing layer was applied, the light would be trapped in the light guide. In the case of a white paint, if no pattern was printed and the whole surface was covered by paint, the output would be dependent on the numerical aperture of the light coupled into the side of the light guide. This may create a hotspot close to the entry point. It is therefore preferable to start the pattern with an area 12a, such as a thin stripe, of no diffusing material for example an area with no diffusing white paint.

Figure 3:
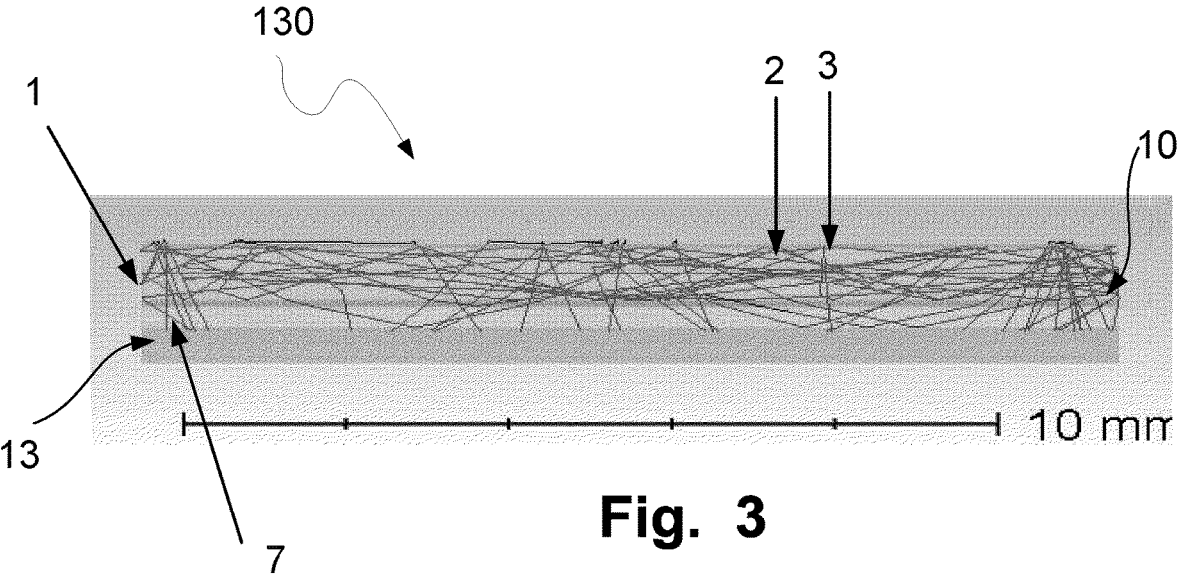
FIG. 3 is illustrating a schematic example of renderings of light travelling in the disclosed device.

FIG. 3 is illustrating a schematic example of renderings 130 of light travelling in the disclosed device. The rendering is based on a diffuser including a light guide 1, a diffusing layer 6 (see FIG. 1), a first layer 2, a reflecting layer 3, and a second layer 7. The total length of the flat white guide is 10 mm and the diffuser is arranged on human skin 13. The edge surface 10 is marked and the light enters the light guide 1 at the opposite side.

For the rendering 130, the principles outlined above regarding differences in refractive indexes between layers have been used. The diffusing layer 6 has a refractive index which is the same refractive index, or at least close to the same refractive index, or higher than the light guide. If a first layer 2 is used, the layer should have a refractive index lower than the refractive index of the light guide 1 to obtain a total internal reflection. In the rendering, an optional second layer 7 is applied between the light guide 1 and the underlying material 13. The second layer 7 should have a refractive index having a lower value than the refractive index of the light guide 1. The second layer 7 may also have a refractive index which is closer to the refractive index of the underlying material 13 than the light guide 1. The second layer 7, may for example be an index matching layer or coating.

In the example of the rendering 130, a trilaminate is considered wherein the trilaminate has three layers with different refractive indexes. The second layer 7 of the rendering 130 does not only provide total internal reflection for some angles in the interface between the light guide 1 and the second layer 7, it also provides an index matching to increase the transmission between the emitting surface of the light guide 1 and the underlying material 13 for the light emitted out from the light emitting surface.

On the top and on the side surfaces, the light guide has a final reflected layer 3 to make sure that light which may be transmitted out of the light guide is reflected back into the light guide.

For the purpose of illustrating the advantages and some of the effects, the layers used for the rendering 130 had the following properties:

| Layer | Refractive index (760 nm) | Thickness | Ref number in FIGS. |
|---|---|---|---|
| Reflector (upper and near side relative light source) | — | — | 3 |
| Carrier | 1.48 | 0.050 mm | 2 |
| Reflector adhesive | 1.474 | 0.038 mm | 2 |
| Diffusing layer | 1.8 | — | 6 |
| Light guide | 1.57 | 0.75 mm | 1 |
| Trilaminate, upper adhesive | 1.474 | 0.062 mm | 7 |
| Trilaminate, carrier | 1.48 | 0.028 mm | 7 |
| Trilaminate, lower adhesive | 1.45 | 0.3 mm | 7 |
| Skin | 1.4 | | (not illustrated) |
| Total | | 1.22 mm | |

The rendering 130 illustrates that areas being coated with a diffusing material reflect incident light with different angles than the angle of incidence. Some of this light may obtain a direction for which it is still trapped in the light guide by total internal reflection and other parts of the light may obtain a direction which allows it to exit the light guide through the light emitting surface.

The rendering 130 also illustrates that the majority of the light that is not reflected in the interface between the light guide 1 and the second layer 2, is refracted and will enter the underlying skin 13. Only a small fraction of the light may reflect in the interface between the second layer 7 and the skin 13. This is due to a good refractive index matching between the second layer and the skin.

As can be seen from the rendering, there is no light that exit the diffuser through any other surfaces than through the emitting surface and through the second layer 7 and into the skin 13.

Rendering 130 is therefore illustrating that the diffuser may provide the advantages of distributing the light over an area with low losses and a high output through the emitting surface.

Figure 4:
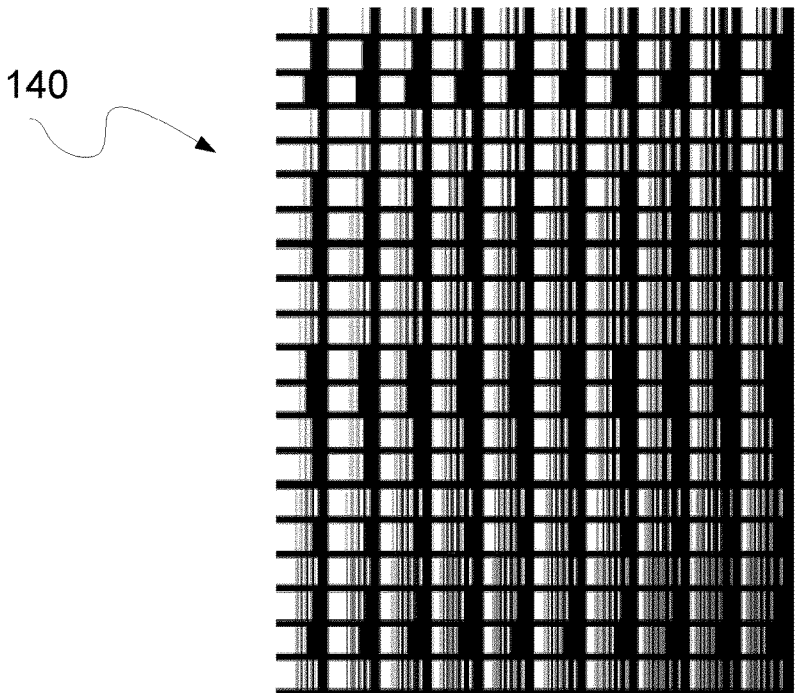
FIG. 4 is illustrating different schematic examples of patterns of diffusing material that could be printed on a flat light guide.

FIG. 4 is illustrating two hundred different schematic examples of patterns of diffusing material 140 that could be printed on a flat light guide, similar to the pattern illustrated in FIG. 3. All of these patterns have varied number of white lines and with varied widths. What the patterns have in common is that they all start with an area of no printing close to where the light is coupled into the light guide and that they end with a larger area of white closer to the edge surface.

Figure 5:
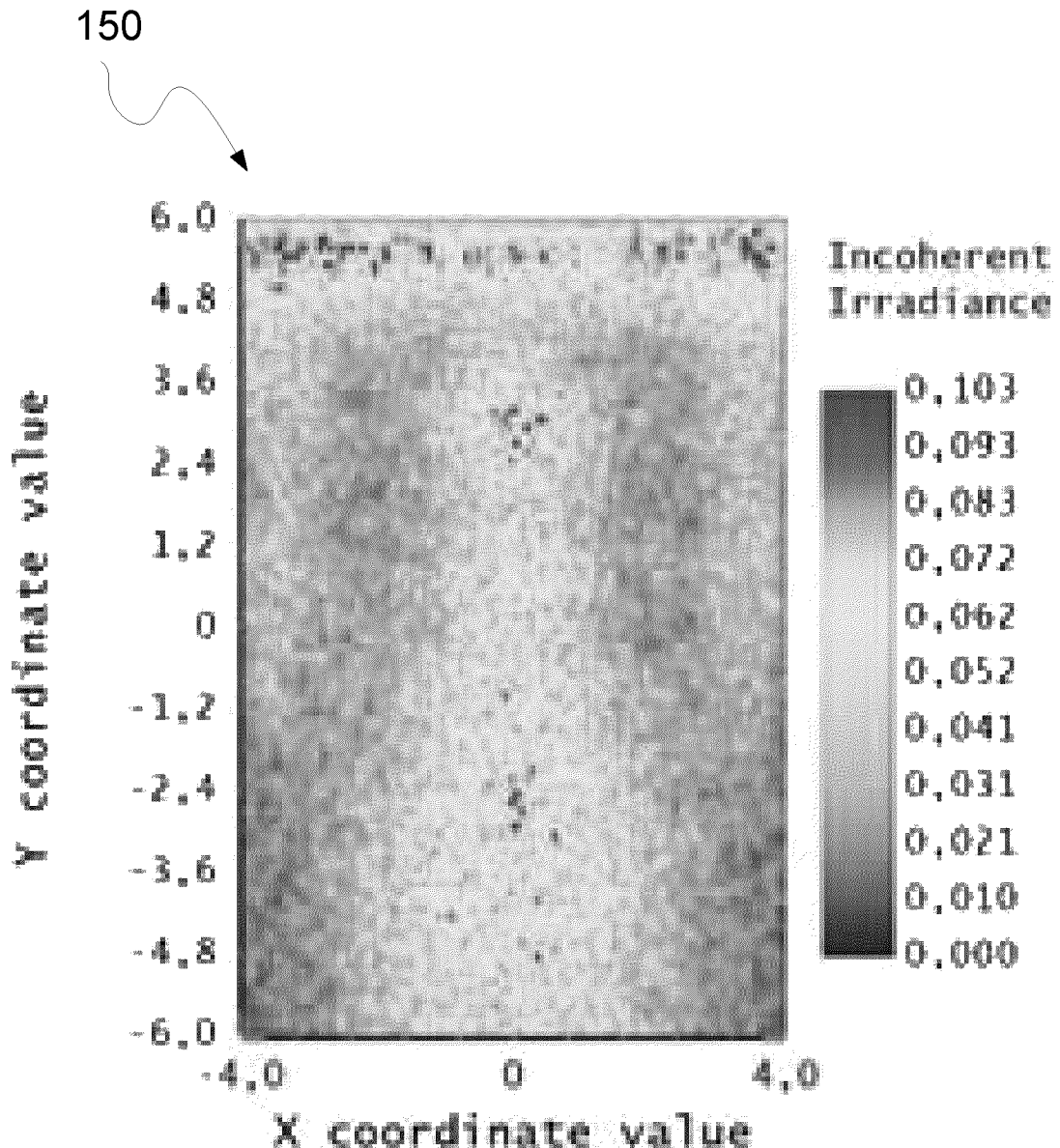
FIG. 5 is illustrating a simulation of light intensity output over an exemplary light emitting surface of the disclosed device.

FIG. 5 is illustrating a simulation of light intensity output 150 over an exemplary light emitting surface of the disclosed device. The light can again be seen to be distributed over the whole area, and hotspots are avoided.

Figures 6A, 6B:
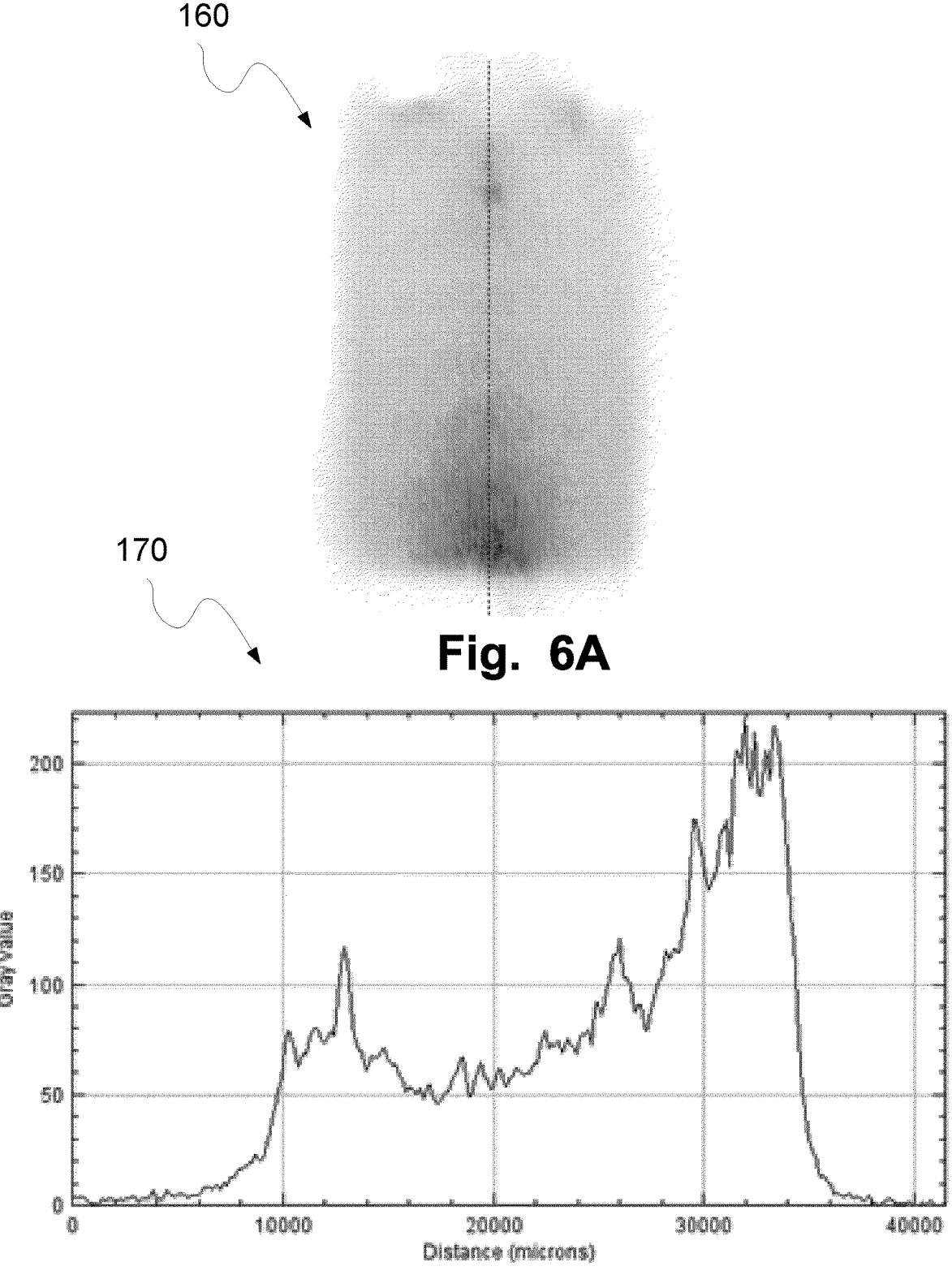
FIGS. 6A and 6B are illustrating a picture showing the intensity over an emitting surface of an exemplary diffuser and the light intensity along the dotted line.

FIGS. 6A and 6B are illustrating a picture 160 showing the intensity over an emitting surface of an exemplary diffuser and the light intensity 170 along the dotted line. FIG. 6A is inverted for better contrast, depicting the light output in a grey scale. Again, this illustrates that the light is spread over the light emitting area and that there is no hotspot provided. It is also seen that the light intensity is low close to where the light is coupled into the diffuser and higher at the opposite end, but still low enough to avoid hotspots which could cause issues during spectroscopic measurements, or damages to the material being measured, such as human tissue, for example human skin.

Figure 7:
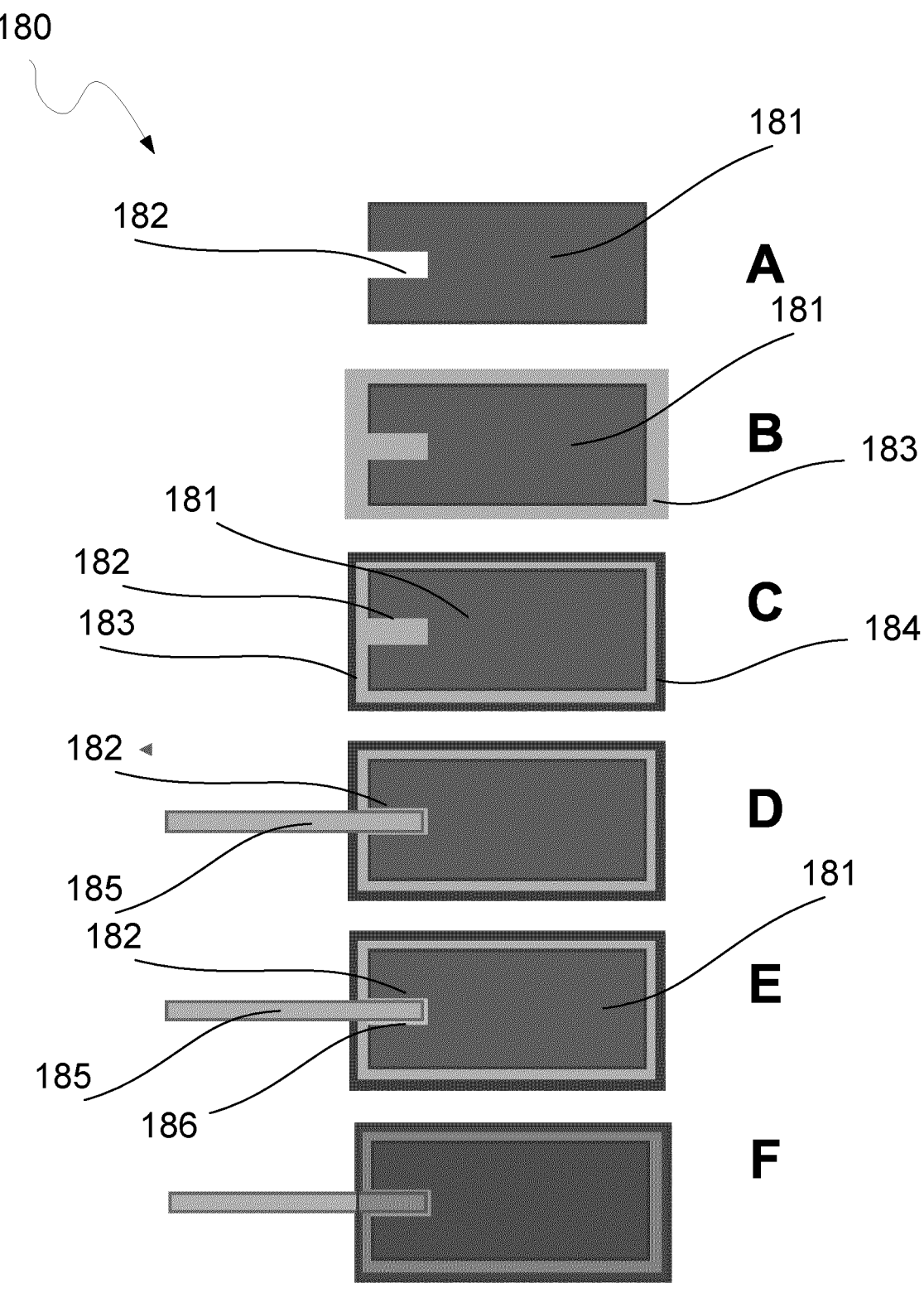
FIG. 7 is illustrating a schematic example of steps for assembling a disclosed device.

FIG. 7 is illustrating a schematic example of steps 180 for assembling a diffuser based on the disclosure herein:

A. Cut out a light guide from a stock material along the side surfaces. The stock material may have the diffusing layer already applied thereon, such as when printing a pattern onto one of the two largest areas. If the diffusing layer is not applied onto the stock material before the cut out, the diffusing layer may be applied after the light guide 181 has been cut out.

If the light is coupled into the diffuser using a waveguide, such as a fiber, a cut-out 182 may be used as a coupling. Other types of light sources may also be arranged in the cut-out 182, such as a LED.

B. An optional first layer 183 may be applied on the top surface, side surfaces and/or emitting surface of the light guide 181. Alternatively, a second layer may be applied on the emitting surface of the light guide 181.

C. Apply a reflecting layer 184 on all sides of the light guide 181, expect for the light emitting surface and where the light may be coupled 182 into the light guide 181. The reflective layer 184 may be made of a metal such as copper tape, chrome tape, and aluminum foil etc, a reflective coating, such as white paint or silver paint. The reflective layer 184 may be made from a single type of reflective material or a combination thereof. The first layer 183 may be used as an adhesive to adhere the reflective layer 184 to the light guide 181, such as when the reflective layer 184 is a metal.

D. Arrange a light source 185 in the coupling 182, for example arranging a waveguide in the cut-out.

E. Attach the light source 185 to the coupling 182, for example by using an adhesive 186, such as a glue. The adhesive has preferably a refractive index that allows a good coupling between the light source 185 and the light guide 181.

F. Arrange the diffuser in a housing. The housing may, for example be made of cured resin. The diffuser may be attached to the housing using a press-fit or an adhesive, such as a glue.

Figure 8:
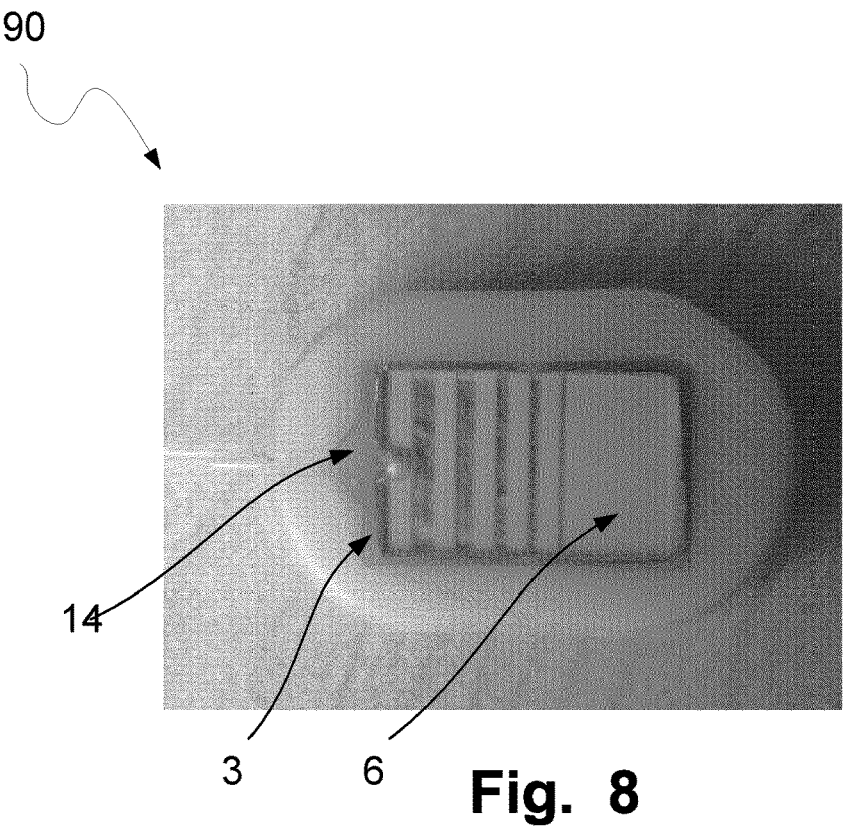
FIG. 8 is illustrating a schematic example of an assembled diffuser.

FIG. 8 is illustrating a schematic example of an assembled diffuser probe 190. In the picture the light emitting surface is seen and through that surface the diffusing layer 6 and reflecting layer 3 are also visible. In the illustrated device, the diffusing layer 6 is a printed white paint, and the reflective layer 6 is a copper tape. The copper tape is seen where no paint is applied on the light guide. This picture also illustrating that the initial part of the light guide 14, close to the waveguide used for coupling light into the diffuser 190, has no diffusing layer 3 applied as the reflective layer 3 is visible.

Figure 9:
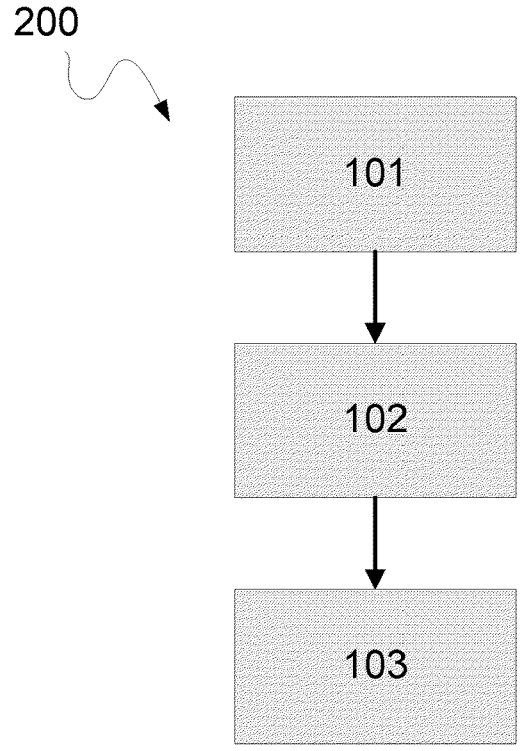
FIG. 9 is illustrating a schematic example a flow-chart for assembling a disclosed device.

FIG. 9 is illustrating a schematic example a flow-chart 200 for a method of assembling a disclosed device. The method includes providing 101 a flat light guide having two larger flat surfaces on opposite sides and side surfaces. One of the two larger flat surfaces being a light emitting surface and the other surface being a back surface. The method may further include arranging 102 a connector for connecting a light to the flat light guide and arranging 103 a diffusing layer in contact with at least one of the two larger flat surfaces of the flat light guide.

The present invention has been described above with reference to specific examples. However, other examples than the above described are equally possible within the scope of the disclosure. Different method steps than those described above may be provided within the scope of the invention. The different features and steps of the invention may be combined in other combinations than those described. The scope of the disclosure is only limited by the appended patent claims.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

The invention claimed is:

1. A device for providing diffuse emission of light through a flat surface, the device comprising:

a flat light guide having two larger flat surfaces on opposite sides and side surfaces, wherein one of the two larger flat surfaces being a light emitting surface and the other of the two larger flat surfaces being a back surface;

a connector for coupling light into said flat light guide; and a diffusing layer arranged on said back surface, and wherein said diffusing layer is arranged as a pattern to provide a plurality of areas of diffuse reflection wherein said plurality of areas are printed stripes applied onto said back surface, said printed stripes have various widths and are spaced apart with non-diffusing areas such that said pattern reduces hotspots, and wherein said printed stripes are unbroken stripes;

a first layer is arranged on top of said diffusing layer having a lower refractive index than said flat light guide, wherein said first layer is a non-diffusing layer for providing internal total reflection in said flat light guide; and wherein said pattern ends with a printed stripe having a comparable larger area at an edge area opposite said connector, and an area of said back surface closest to said connector has no printed stripe.

2. The device of claim 1, wherein a reflective material is arranged on all sides of the flat light guide apart from said light emitting surface.

3. The device of claim 2, wherein said reflective material reflects light either through specular reflection or through diffuse reflection.

4. The device of claim 2, wherein the diffusing layer is arranged between said back surface and said reflective material.

5. The device of claim 2, wherein said diffusing layer is arranged on said back surface and said first layer is arranged between said diffusing layer and said reflective material.

6. The device of claim 1, wherein the diffusing layer has a refractive index higher than said flat light guide.

7. The device of claim 1, wherein said diffusing layer is printed on said back flat surface of said flat light guide.

8. The device of claim 1, wherein said diffusing layer is arranged as said pattern on said back surface of said flat light guide and said reflective layer is reflecting light of areas of said back surface not covered by said pattern.

9. The device of claim 1, wherein said light emitting surface is covered by a second layer having a lower refractive index than said flat light guide.

10. The device of claim 1, wherein a further diffusing layer is arranged on said light emitting surface, or is arranged in said light guide.

11. The device of claim 1, wherein an initial area closest to said connector is not covered by said diffusing layer.

12. A method of manufacturing a device for providing diffuse emission of light through a flat surface, comprising:

providing a flat light guide having two larger flat surfaces on opposite sides and side surfaces, wherein one of the two larger flat surfaces being a light emitting surface and the other of the two larger flat surfaces being a back surface;

arranging a connector for coupling light into said flat light guide;

arranging a diffusing layer in contact with said back surface of said flat light guide, wherein said diffusing layer is applied onto said back surface by printing and is being arranged as a pattern providing a plurality of areas of diffuse reflection wherein said plurality of areas are printed stripes with various widths and spaced apart with non-diffusing areas such that said pattern reduces hotspots, and wherein said printed stripes are unbroken stripes; and arranging a first layer on top of said diffusing layer wherein said first layer has a lower refractive index than said flat light guide, and wherein said first layer is a non-diffusing layer for providing internal total reflection; and wherein said pattern ends with a printed stripe having a comparable larger area at an edge area opposite said connector, and an area of said back surface closest to said connector has no printed stripe.

* * * * *